United States Patent [19]

Spitz et al.

[11] 3,999,551
[45] Dec. 28, 1976

[54] SUBCUTANEOUS GUIDE ASSEMBLY

[75] Inventors: Eugene B. Spitz; Richard E. Brenz, both of Media; Charles C. Hansford, Chester Township, all of Pa.

[73] Assignee: Bio-Medical Research, Ltd., Lima, Pa.

[22] Filed: Jan. 7, 1975

[21] Appl. No.: 539,221

[52] U.S. Cl. .............................. 128/303 R; 403/19; 403/44
[51] Int. Cl.² ......................................... A61B 17/00
[58] Field of Search ............... 16/110.5; 128/303 R, 128/341, 347, 349 R, 350, 356; 403/19, 44

[56] References Cited
UNITED STATES PATENTS

| 512,384 | 1/1894 | Meacham | 403/44 X |
|---|---|---|---|
| 1,002,992 | 9/1911 | Humphreys | 16/110.5 X |
| 2,127,163 | 8/1938 | Davis | 16/110.5 X |
| 2,532,093 | 11/1950 | Golub et al. | 16/110.5 X |
| 2,788,787 | 4/1957 | Trace | 128/303 R |
| 2,905,178 | 9/1959 | Hilzinger | 128/303 R |
| 2,918,919 | 12/1959 | Wallace | 128/350 R X |
| 3,045,676 | 7/1962 | Slaten | 128/303 R |
| 3,137,298 | 6/1964 | Glassman | 128/328 |
| 3,185,155 | 5/1965 | Slaten et al. | 128/303 R |
| 3,314,431 | 4/1967 | Smith, Jr. | 128/341 X |
| 3,640,281 | 2/1972 | Robertson | 128/349 R X |
| 3,656,486 | 4/1972 | Robertson | 128/349 R X |
| 3,866,609 | 2/1975 | Sparks | 128/303 R |

Primary Examiner—Channing L. Pace
Attorney, Agent, or Firm—Paul Maleson; Morton J. Rosenberg

[57] ABSTRACT

A subcutaneous guide assembly for use by surgeons during an operation where surgical elements must be passed through an elongated path internal to a human body. The guide assembly includes an elongated rod of predetermined contour and length which is secured on opposing ends to a handle member and to one of a variety of surgical elements which may be releasably secured to the rod through threaded engagement. Additionally, a plurality of rod members of differing lengths and contours may be easily secured to the handle section of the subcutaneous guide assembly. The handle section includes an internal chamber where various surgical elements may be contained for use in particular portions or phases of an operation. The handle further includes a mechanism whereby the contained surgical elements within the handle internal chamber may be easily sterilized.

12 Claims, 11 Drawing Figures

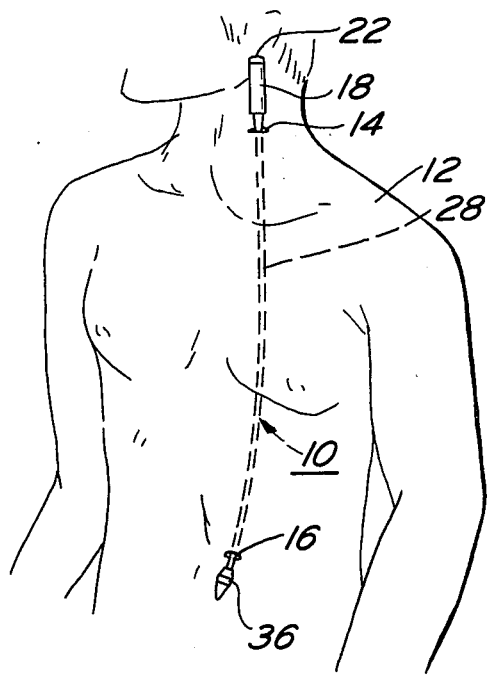
FIG. 1
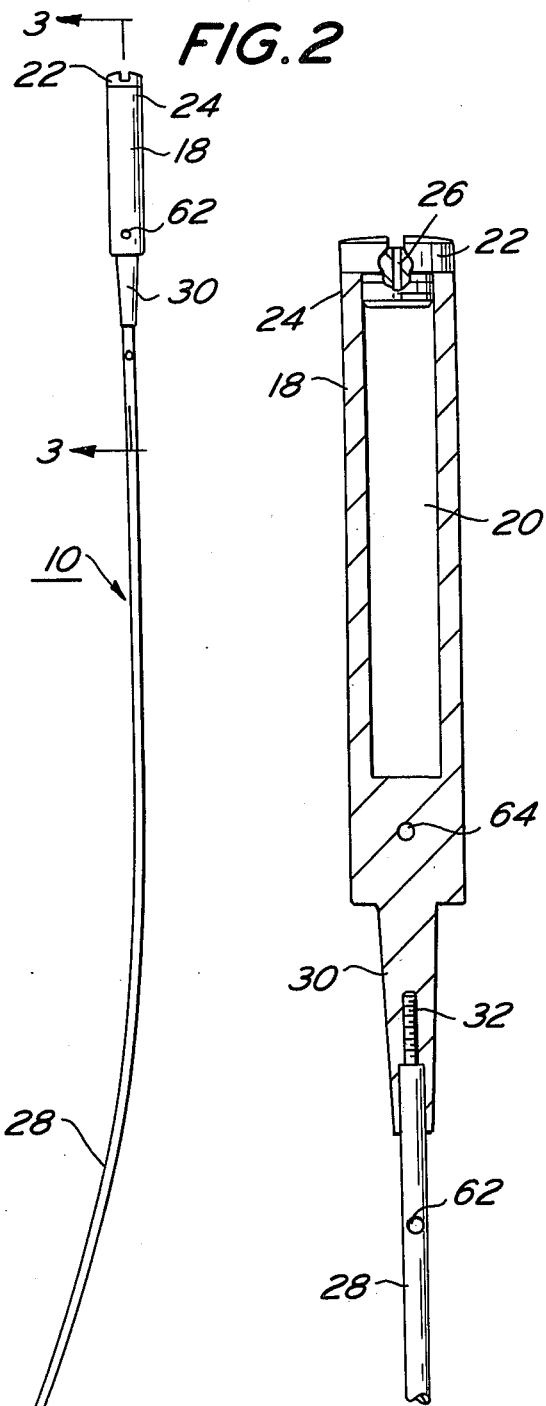
FIG. 2
FIG. 3
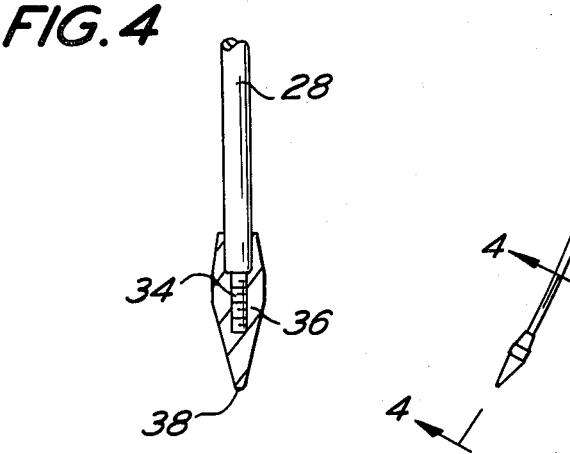
FIG. 4

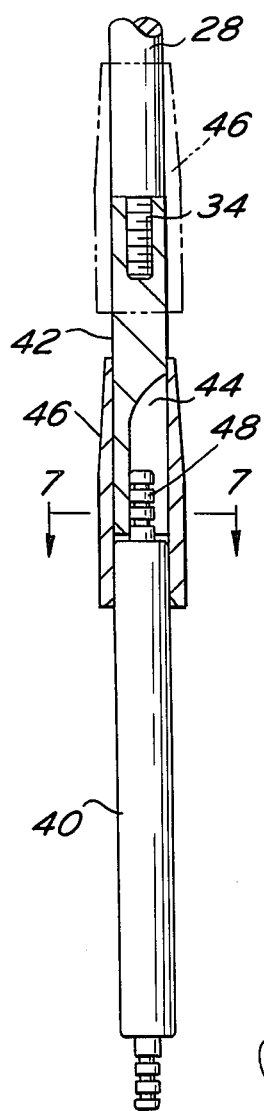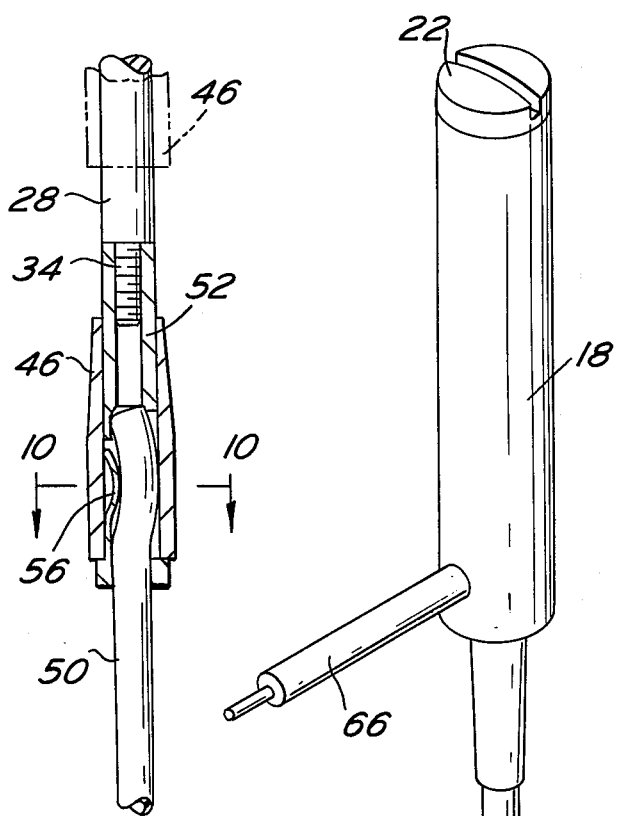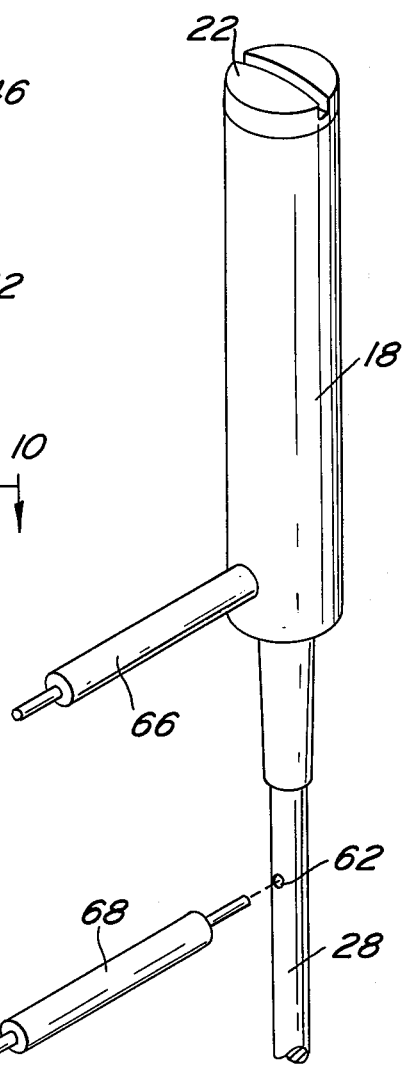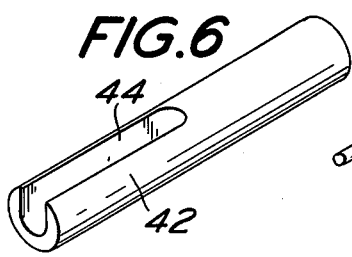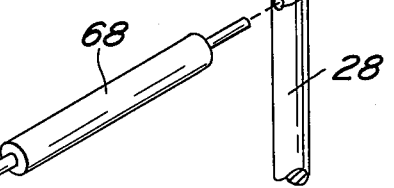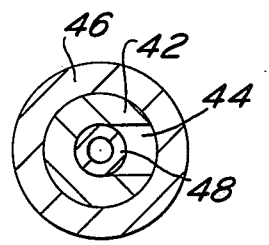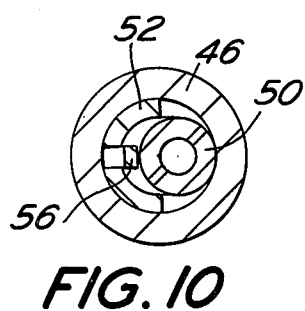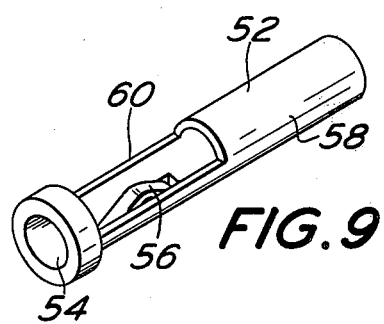

SUBCUTANEOUS GUIDE ASSEMBLY

BACKGROUND OF THE INVENTION

1. FIELD OF THE INVENTION

This invention relates to subcutaneous guide assemblies for use in surgical operations. In particular, this invention pertains to assemblies for implantation or displacement of surgical elements internal to the body from a first position to a second position. More in particular, this invention relates to subcutaneous guide assemblies utilized in operations of the hydrocephalus type.

2. PRIOR ART

In general, where surgical elements are to be placed internal to the human body throughout an extended length, an incision throughout the length of the implantation path has been utilized. This has caused increased infection rates and has materially affected the success ratio of various operations. Additionally, incisions of this length and resulting implantation procedures generally take extended periods of time which has also affected the success ratio of such operations.

Some prior surgical instruments do provide for implantation of various surgical elements beneath the skin of the human body. However, in some of these instruments, the range of movement and implantation is severely limited due to the fact that such instruments are adapted to only provide insertion of the surgical elements in a predetermined area. Additionally, such prior instruments are not adapted for quick release mechanisms to provide securement and release of the surgical element and the implantation device. Thus, such instruments are lacking in versatility when taken with respect to implantation techniques necessary for various operations. Often, in operations of the hydrocephalus type, valve elements and as well as flexible tubing must be passed through extended portions of the body. Instruments of the aforementioned type do not provide for quick and efficient placement of the necessary surgical elements.

SUMMARY OF THE INVENTION

A subcutaneous guide assembly to be passed internal a human body from a first opening in a first positional location of the body to a neighborhood of a second opening in a second positional location of the body. The subcutaneous guide assembly includes a handle having an internal chamber with a cap releasably secured to a first end of the handle. The cap has at least one opening passing therethrough in communication with the internal chamber of the handle. The guide assembly includes a guide element which is releasably secured to a second end of the handle. The guide element forms an elongate rod member having a predetermined contour which is adaptable for passage through the body from the first to the second opening.

BRIEF DESCRIPTION OF THE DRAWINGS

FIG. 1 is a perspective view of the subcutaneous guide assembly inserted within a human body;

FIG. 2 is an elevation view of the subcutaneous guide assembly having a connector cap attached to a lower end of the guide element;

FIG. 3 is a sectional view of the handle of the subcutaneous guide assembly taken along the section line 3—3 of FIG. 2;

FIG. 4 is a sectional view of the lower end of the subcutaneous guide assembly showing the connector cap and taken along the section line 4—4 of FIG. 2;

FIG. 5 is an elevational view of the lower end of the subcutaneous guide assembly showing a holding element for a valve;

FIG. 6 is a perspective view of the valve holding element;

FIG. 7 is a sectional view of the valve holding element taken along the section line 7—7 of FIG. 5;

FIG. 8 is an elevation view of a lower end of the subcutaneous guide assembly showing a tubular locking element holding a flexible tube in secured engagement with the guide assembly;

FIG. 9 is a perspective view of the tubular locking element;

FIG. 10 is a sectional view of the subcutaneous guide assembly taken along the section line 10—10 of FIG. 8; and, FIG. 11 is a perspective view of an upper portion of the handle portion of the subcutaneous guide assembly showing the handle release elements.

DESCRIPTION OF THE PREFERRED EMBODIMENTS

Referring now to FIG. 1–3 there is shown subcutaneous guide assembly 10 to be passed internal through a portion of human body 12. Guide assembly 10 may in general be used to assist in the implantation of various surgical devices within body 12 which are to be positionally located remote from a first opening 14. Through use of guide assembly 10 as is herein described, assembly 10 may be inserted in first opening 14 and passed internal to human body 12 to a second opening 16 where various surgical elements may be attached. Assembly 10 may then be withdrawn from first opening 14 thereby guiding the necessary elements through the interior of human body 12 without the necessity of implantation by incising the body throughout the path contour passed through by subcutaneous guide assembly 10. In particular, assembly 10 has been successfully utilized for predetermined positional implantation of surgical devices used in the control of hydrocephalus.

In overall concept, subcutaneous guide assembly 10 includes handle section 18 which during the operation generally remains external to human body 12 throughout a particular guiding action or implantation. Handle section 18 is generally cylindrical in nature and is of sufficient diameter to be easily manipulatable under manual control by a surgeon during that phase of the operation in which guide assembly 10 is used. Handle 18 includes internal chamber 20 formed in generally a cylindrical geometric contour and being of sufficient size and volume to incorporate various surgical elements therein, such surgical elements to be further described in following paragraphs and are included in the overall assembly 10. In general, handle 18 is formed of stainless steel or some like material which permits sterilization without a derogatory chemical reaction with a sterilizing environment.

To enclose internal chamber 20, cap 22 is releasably secured to handle first end 24. As is seen, cap 22 is threadedly secured to first end 24 to permit reversible securement therebetween. Cap 22 includes at least one through opening 26 which is in communication with the external environment on the one end and internal chamber 20 on an opposing end. In this way, when surgical elements are contained within internal chamber 20, they may be easily sterilized and provide a fluid communication path to the external sterilizing atmosphere.

Guide element 28 is releasably secured to handle second end 30. In particular, guide element 28 forms an elongated rod member having a predetermined contour adaptable for passage through human body 12 from first opening 14 to second opening 16. Guide element 28 may be of varying elongate lengths as well as differing geometric contours which may be determined by body size as well as positional placement of first opening 14 and second opening 16 necessary for a particular operation phase. The overall contour and length of guide element 28 may be determined from a number of parameters which are generally empirically derived to provide for easy passage of guide element 28 through a portion of human body 12 without causing abrasive or injurious contact with internal organs of human body 12. Guide element 28 is generally formed of stainless steel or some like material and is generally releasably secured to handle second end 30 by threaded engagement of guide element 28 with handle second end 30 as is shown by threaded section 32 in FIG. 3. In this manner, handle section 18 is adaptable for releasable securement to a plurality of guide elements having differing lengths and contours as is necessary to a particular operation or phase of an operation. The concept of threaded engagement of guide element 28 with handle 18 is of particular importance in that such optimizes the time for removal as well as securement between element 28 and handle 18 during an operation wherein the time factor for changing elements 28 may be of critical importance for the welfare of the patient.

As is shown in FIG. 4, guide element 28 includes lower threaded section 34 which permits releasable securement mechanism for a variety of surgical elements which may be used during the operation. In the initial phase of the operation where assembly 10 is to be passed from first opening 14 to second opening 16 connector cap 36 is releasably secured to a lower end of guide element 28 at lower threaded section 34 distal from handle second end 30. Connector cap 36 includes a rounded end section or blunt nose 38 to prevent abrasive contact with internal organs of human body 12 as guide assembly 10 is passed therethrough.

Referring now to FIG. 5, 6 and 7 there are shown guide assembly 10 elements utilized for rigidly engaging elongate element or hydrocephalus valve 40, which may be of the type generally shown and described in U.S. Pat. No. 2,969,066. Holding element 42 is generally cylindrical in nature and includes groove 44 which passes partially throughout the extended length of holding element 42 as is shown in FIG. 6. The diameter of groove 44 is of sufficient size to accept the insertion of a portion of elongate element 40 as is shown in FIG. 5. Holding element 42 is releasably secured to lower threaded section 34 of guide element 28. In general, holding element 42 has an external diameter which is substantially equal to the diameter of the guide element 28. Sleeve member 46, having an internal through diameter substantially equal to but slightly greater than the diameter of holding element 42 and guide element 28 is slidably movable on guide element 28 and holding element 42. When valve stem 48 is inserted into groove 44, the peripheral boundary of valve 40 extends slightly outwardly from the periphery of holding element 42. Thus, sleeve member 46 may be passed in a downward direction as shown in FIG. 5 into frictional engagement with elongate element 40 when elongate element 40 is at least partially inserted in groove 44. Elongate member 40 then is frictionally engaged between holding element 42 and sleeve member 46. The surgeon may then retract guide assembly 10 through second opening 16 for positional placement of elongate element 40 in the neighborhood of first opening 14.

In some cases, as is shown in FIGS. 8, 9 and 10, subcutaneous guide assembly 10 may be utilized for passing flexible tubing 50 through a predetermined portion of body 12. In this embodiment, tubular latch element 52 being generally cylindrical in nature and having an external diameter substantially equal to guide element 28 is threadedly secured at lower threaded section 34 to guide element 28. Through opening 54 passes generally in the axial direction of tubular latch element 52 as is shown in FIG. 9. Through opening 54 is of sufficient diameter to accept flexible tubing 50 in a manner as shown in FIG. 8. Tubular latch element 52 includes tongue member 56 formed in side wall 58 and which extends internally into through opening 54 of tubular lock element 52. Side wall cutout section 60 as is shown in FIG. 9 is located in an opposing direction to tongue member 56 and provides for flexible tubing 50 after insertion into opening 54 to be passed partially external to tubular latch element 52 when flexible tubing 50 is contacted by tongue member 56. In order to frictionally engage tubing 50, sleeve member 46 as has been previously described is passed in a downward direction as shown by FIG. 8 to pass over tubular lock element 52 and frictionally engage tubing 50 between tongue 56 and an inner surface of sleeve member 46. Thus, assembly 10 may be utilized to withdraw flexible tubing 50 from second opening 16 to a predetermined positional location in the neighborhood of first opening 14 on body 12.

In order to facilitate releasable securement between handle 18 and guide element 28, through opening 62 and 64 are respectively located in guide element 28 and handle section 18 as is shown in FIGS. 3 and 11. Openings 62 and 64 have a diameter sufficient to accept insertion of stems of handle release elements 66 and 68 as is shown in FIG. 11. Thus, in order to provide release of handle 18 from guide element 28 handle rod member 66 may be at least partially inserted within a side wall of handle 18 while concurrently guide rod member 68 is at least partially inserted within a side wall of guide element 28. Guide rod member 68 and handle rod member 66 may then be rotated in opposing directions for either threaded release of guide element 28 and handle 18 or if in an opposing rotatable direction for securement therebetween.

What is claimed is:
1. A subcutaneous guide assembly adapted to be passed internal a human body from a first opening in a first positional location of said body to a neighborhood of a second opening in a second positional location of said body comprising:
   a. handle means having an internal chamber;
   b. cap means releaseably secured to a first end of said handle means, said cap means having at least one opening passing therethrough in communication with said internal chamber for selective communication with an external sterilizing chamber; and,
   c. a guide element releasably secured to a second end of said handle means, said guide element forming an elongated, inflexible, and substantially solid rod member having having a predetermined inflexible arcuate contour adaptable for passage through said body from said first to said second opening.

2. The subcutaneous guide assembly as recited in claim 1 where said guide element is threadedly secured to a second end of said handle means, said handle means being thereby adaptable for selective releasable securement to a plurality of said guide elements having differing lengths.

3. The subcutaneous guide assembly as recited in claim 2 including connector cap means releasably secured to an end of said guide element distal from said handle second end, said connector cap means having a rounded end section to prevent abrasive contact with internal organs of said body.

4. The subcutaneous guide assembly as recited in claim 3 where said connector cap means is threadedly secured to said guide element.

5. The subcutaneous guide assembly as recited in claim 2 including:
 a. holding means releasably secured to an end section of said guide element, said holding means having a groove formed therein;
 b. an elongate element at least partially inserted within said groove of said holding means; and,
 c. a sleeve member slidably moveable on said guide element and said holding means, and having a first positional location said holding means for frictionally engaging said elongate element between said holding means and said sleeve member when said elongate element is at least partially inserted in said groove, and a second positional location adjacent said guide means in which said sleeve member is frictionally disengaged from said elongate member.

6. The subcutaneous guide assembly as recited in claim 5 where said holding means is threadedly secured to an end section of said guide element distal from said handle means second end.

7. The subcutaneous guide assembly as recited in claim 2 including:
 a. tubular latching means releasably secured to an end section of said guide element, said tubular latching means having an opening adapted to receive a flexible tube; and,
 b. a sleeve member slidably moveably on said guide element and said tubular latching means, and having a downward position on said tubular latching means in which said sleeve member frictionally engages said flexible tube between said tubular latching means and said sleeve member when said flexible tube is at least partially inserted in said tubular locking means opening, and another position on said guide means in which said sleeve member does not frictionally engage said flexible tube.

8. The subcutaneous guide assembly as recited in claim 7 where said tubular latching means includes a tongue member formed in a sidewall of said tubular latching means, said tongue member extending internal said tubular latching means.

9. The subcutaneous guide assembly as recited in claim 8 where said tubular latching means includes a sidewall cut-out section located opposing said tongue member for providing said flexible tubing to pass partially external to said tubular latching means when said tubing is contacted by said tongue member.

10. The subcutaneous guide assembly as recited in claim 9 where said sleeve member frictionally engages said flexible tubing passing through said sidewall cut-out section to maintain securement of said tubing between said tubular latching means and said sleeve member.

11. The subcutaneous guide assembly as recited in claim 10 where said tubular latching means is threadedly secured to an end section of said guide element distal to said handle means second end.

12. The subcutaneous guide assembly as recited in claim 1 where said handle means, said cap means, and said guide element are formed of stainless steel, said handle and said guide element each having a transverse hole, said hole in said guide element being provided adjacent said end thereof secured to said handle, and handle release means being provided for selective insertion in each of said holes, said handle release means each comprising a non-threaded handle rod member selectively and non-latchably insertable into each of said holes to provide hand grips to aid in threadedly releasing said handle means from said guide element.

* * * * *